United States Patent
Alpini et al.

(10) Patent No.: US 8,636,690 B2
(45) Date of Patent: Jan. 28, 2014

(54) CATHETER BALLOONS WITH INTEGRATED NON-DISTENSIBLE SEALS

(75) Inventors: Alfred A. Alpini, Landenberg, PA (US); Carey V. Campbell, Flagstaff, AZ (US); Sherif Eskaros, Elkton, MD (US); David R. King, Lake Como, NJ (US); Joseph E. Korleski, Jr., Newark, DE (US); James William Mann, Elkton, MD (US); Lonzo C. McLaughlin, Middletown, DE (US); Kenneth Newcomb, Wilmington, DE (US); Peter J. Roeber, Wallingford, PA (US)

(73) Assignee: W. L. Gore & Associates, Inc., Newark, DE (US)

( * ) Notice: Subject to any disclaimer, the term of this patent is extended or adjusted under 35 U.S.C. 154(b) by 393 days.

(21) Appl. No.: 12/610,535

(22) Filed: Nov. 2, 2009

(65) Prior Publication Data

US 2010/0049123 A1  Feb. 25, 2010

Related U.S. Application Data

(62) Division of application No. 11/501,149, filed on Aug. 7, 2006, now abandoned.

(51) Int. Cl.
*A61M 29/00* (2006.01)

(52) U.S. Cl.
USPC .................. 604/103; 604/96.01; 604/101.05; 604/103.06

(58) Field of Classification Search
USPC .................. 604/96.01, 101.01–101.05, 103, 604/103.05, 103.06, 103.07, 103.11, 604/103.12, 509, 912, 915–917
See application file for complete search history.

(56) References Cited

U.S. PATENT DOCUMENTS

| | | | |
|---|---|---|---|
| 1,690,995 | A | 11/1928 | Pratt |
| 3,640,282 | A | 2/1972 | Kamen |
| 3,746,003 | A | 7/1973 | Blake et al. |
| 3,953,566 | A | 4/1976 | Gore |
| 4,003,382 | A | 1/1977 | Dyke |
| 4,106,509 | A | 8/1978 | McWhorter |
| 4,187,390 | A | 2/1980 | Gore |
| 4,194,041 | A | 3/1980 | Gore et al. |
| 4,279,245 | A | 7/1981 | Takagi et al. |
| 4,280,500 | A | 7/1981 | Ono |
| 4,304,010 | A | 12/1981 | Mano |

(Continued)

FOREIGN PATENT DOCUMENTS

| EP | 0 372 088 | 6/1990 |
|---|---|---|
| EP | 0 540 858 | 5/1993 |

(Continued)

OTHER PUBLICATIONS

Dillon M E, Silicone and Poly (tetrafluoroethylene) Interpenetrating Polymer Networks, 1994 American Chemical Society.

*Primary Examiner* — Kami A Bosworth
(74) *Attorney, Agent, or Firm* — David J. Johns; Katherine L. Carleton

(57) ABSTRACT

A catheter balloon with integral non-distending regions having a plurality of layers which wind around the balloon material and overlap to form an angle of between 45 and 90 degrees relative to each other upon inflation, and methods of making the non-distending regions are provided.

6 Claims, 5 Drawing Sheets

(56) References Cited

U.S. PATENT DOCUMENTS

| | | |
|---|---|---|
| 4,327,736 A | 5/1982 | Inoue |
| 4,338,942 A | 7/1982 | Fogarty |
| 4,403,612 A | 9/1983 | Fogarty |
| 4,443,511 A | 4/1984 | Worden et al. |
| 4,490,421 A | 12/1984 | Levy |
| 4,573,966 A | 3/1986 | Weikl et al. |
| 4,596,839 A | 6/1986 | Peters |
| 4,608,984 A | 9/1986 | Fogarty |
| 4,613,544 A | 9/1986 | Burleigh |
| 4,619,641 A | 10/1986 | Schanzer |
| 4,637,396 A | 1/1987 | Cook |
| 4,650,466 A | 3/1987 | Luther |
| 4,702,252 A | 10/1987 | Brooks et al. |
| 4,706,670 A | 11/1987 | Andersen et al. |
| 4,713,070 A | 12/1987 | Mano |
| 4,737,219 A | 4/1988 | Taller et al. |
| 4,739,762 A | 4/1988 | Palmaz |
| 4,743,480 A | 5/1988 | Campbell et al. |
| 4,764,560 A | 8/1988 | Mitchell |
| 4,816,339 A | 3/1989 | Tu et al. |
| 4,819,751 A | 4/1989 | Shimada et al. |
| 4,832,688 A | 5/1989 | Sagae et al. |
| 4,896,669 A | 1/1990 | Bhate et al. |
| 4,946,464 A | 8/1990 | Pevsner |
| 4,955,899 A | 9/1990 | Della Coma et al. |
| 5,041,047 A | 8/1991 | Casale |
| 5,061,276 A | 10/1991 | Tu et al. |
| 5,066,298 A | 11/1991 | Hess |
| 5,071,609 A | 12/1991 | Tu et al. |
| 5,087,244 A | 2/1992 | Wolinsky et al. |
| 5,100,429 A | 3/1992 | Sinofsky et al. |
| 5,108,370 A | 4/1992 | Walinsky |
| 5,112,304 A | 5/1992 | Barlow et al. |
| 5,116,318 A | 5/1992 | Hillstead |
| 5,137,512 A | 8/1992 | Burns et al. |
| 5,147,302 A | 9/1992 | Euteneuer et al. |
| 5,152,782 A | 10/1992 | Kowligi et al. |
| 5,171,297 A | 12/1992 | Barlow et al. |
| 5,192,296 A | 3/1993 | Bhate et al. |
| 5,195,970 A | 3/1993 | Gahara |
| 5,197,978 A | 3/1993 | Hess |
| 5,201,706 A | 4/1993 | Noguchi et al. |
| 5,211,654 A | 5/1993 | Kaltenbach |
| 5,213,576 A | 5/1993 | Abiuso et al. |
| 5,226,880 A | 7/1993 | Martin |
| 5,236,659 A | 8/1993 | Pinchuk et al. |
| 5,254,090 A | 10/1993 | Lombardi et al. |
| 5,256,143 A | 10/1993 | Miller et al. |
| 5,286,254 A | 2/1994 | Shapland et al. |
| 5,290,306 A | 3/1994 | Trotta et al. |
| 5,304,120 A | 4/1994 | Crandell et al. |
| 5,304,214 A | 4/1994 | DeFord et al. |
| 5,304,340 A | 4/1994 | Downey |
| 5,308,356 A | 5/1994 | Blackshear |
| 5,330,429 A | 7/1994 | Noguchi et al. |
| 5,338,299 A | 8/1994 | Barlow |
| 5,342,305 A | 8/1994 | Shonk |
| 5,342,348 A | 8/1994 | Kaplan |
| 5,348,538 A | 9/1994 | Wang et al. |
| 5,358,486 A | 10/1994 | Saab |
| 5,358,516 A | 10/1994 | Myers et al. |
| 5,366,442 A | 11/1994 | Wang et al. |
| 5,366,472 A | 11/1994 | Hillstead |
| 5,370,618 A | 12/1994 | Leonhardt |
| 5,403,340 A | 4/1995 | Wang et al. |
| 5,409,495 A | 4/1995 | Osborn |
| 5,415,636 A | 5/1995 | Forman |
| 5,425,710 A | 6/1995 | Khair et al. |
| 5,429,605 A | 7/1995 | Richling |
| 5,456,661 A | 10/1995 | Narciso |
| 5,458,568 A | 10/1995 | Racchini et al. |
| 5,458,605 A | 10/1995 | Klemm |
| 5,466,252 A | 11/1995 | Soukup et al. |
| 5,470,313 A | 11/1995 | Crocker et al. |
| 5,470,314 A | 11/1995 | Walinsky |
| 5,476,589 A | 12/1995 | Bacino |
| 5,478,320 A | 12/1995 | Trotta |
| 5,478,349 A | 12/1995 | Nicholas |
| 5,484,411 A | 1/1996 | Inderbitzen et al. |
| 5,490,839 A | 2/1996 | Wang et al. |
| 5,496,276 A | 3/1996 | Wang et al. |
| 5,498,238 A | 3/1996 | Shapland et al. |
| 5,499,973 A | 3/1996 | Saab |
| 5,499,980 A | 3/1996 | Euteneuer |
| 5,499,995 A | 3/1996 | Teirstein |
| 5,500,180 A | 3/1996 | Anderson et al. |
| 5,500,181 A | 3/1996 | Wang et al. |
| 5,512,051 A | 4/1996 | Wang et al. |
| 5,519,172 A | 5/1996 | Spencer et al. |
| 5,527,282 A | 6/1996 | Segal |
| 5,529,820 A | 6/1996 | Nomi et al. |
| 5,571,089 A | 11/1996 | Crocker |
| 5,609,605 A | 3/1997 | Marshall et al. |
| 5,613,979 A | 3/1997 | Trotta et al. |
| 5,620,649 A | 4/1997 | Trotta |
| 5,641,373 A | 6/1997 | Shannon et al. |
| 5,645,560 A | 7/1997 | Crocker et al. |
| 5,647,848 A | 7/1997 | Jorgensen |
| 5,716,340 A | 2/1998 | Schweich et al. |
| 5,716,396 A | 2/1998 | Williams, Jr. |
| 5,752,934 A | 5/1998 | Campbell et al. |
| 5,766,201 A | 6/1998 | Ravenscroft et al. |
| 5,797,877 A | 8/1998 | Hamilton et al. |
| 5,807,327 A | 9/1998 | Green et al. |
| 5,843,116 A | 12/1998 | Crocker et al. |
| 5,868,704 A | 2/1999 | Campbell et al. |
| 5,868,708 A | 2/1999 | Hart et al. |
| 5,893,840 A | 4/1999 | Hull et al. |
| 5,908,406 A | 6/1999 | Ostapchenko et al. |
| 5,944,734 A | 8/1999 | Hermann et al. |
| 5,951,941 A | 9/1999 | Wang et al. |
| 5,954,745 A | 9/1999 | Gertler et al. |
| 5,972,441 A | 10/1999 | Campbell |
| 6,010,480 A | 1/2000 | Abele et al. |
| 6,013,092 A | 1/2000 | Dehdashtian |
| 6,027,779 A | 2/2000 | Campbell et al. |
| 6,048,356 A | 4/2000 | Ravenscroft et al. |
| 6,120,477 A | 9/2000 | Campbell et al. |
| 6,132,824 A | 10/2000 | Hamlin |
| 6,234,995 B1 | 5/2001 | Peacock, III |
| 6,287,290 B1 | 9/2001 | Perkins et al. |
| 6,287,314 B1 | 9/2001 | Lee et al. |
| 6,319,249 B1 | 11/2001 | Tollner |
| 6,319,259 B1 | 11/2001 | Lee et al. |
| 6,319,529 B1 | 11/2001 | Thompson |
| 6,336,937 B1 | 1/2002 | Vonesh et al. |
| 6,375,637 B1 | 4/2002 | Campbell et al. |
| 6,428,506 B1 | 8/2002 | Simhambhatla et al. |
| 6,482,348 B1 | 11/2002 | Wang et al. |
| 6,488,688 B2 | 12/2002 | Lim et al. |
| 6,572,813 B1 | 6/2003 | Zhang et al. |
| 6,602,224 B1 | 8/2003 | Simhambhatla |
| 6,663,646 B1 | 12/2003 | Shah |
| 6,746,425 B1 | 6/2004 | Beckham |
| 6,756,094 B1 | 6/2004 | Wang et al. |
| 6,887,227 B1 | 5/2005 | Barbut |
| 6,890,395 B2 | 5/2005 | Simhambhatla |
| 6,905,743 B1 | 6/2005 | Chen et al. |
| 6,923,827 B2 | 8/2005 | Campbell et al. |
| 6,939,593 B2 | 9/2005 | Wang |
| 6,977,103 B2 | 12/2005 | Chen et al. |
| 7,052,507 B2 | 5/2006 | Wakuda et al. |
| 7,195,638 B1 | 3/2007 | Sridharan |
| 7,279,208 B1 | 10/2007 | Goffena et al. |
| 7,306,729 B2 | 12/2007 | Bacino et al. |
| 7,625,337 B2 | 12/2009 | Campbell et al. |
| 7,785,290 B2 | 8/2010 | Alpini et al. |
| 2001/0008970 A1 | 7/2001 | Ravenscroft et al. |
| 2002/0087165 A1 | 7/2002 | Lee et al. |
| 2002/0163104 A1 | 11/2002 | Motsenbocker |
| 2003/0074016 A1 | 4/2003 | Campbell et al. |
| 2003/0083687 A1 | 5/2003 | Paliazza |
| 2003/0088209 A1 | 5/2003 | Chiu et al. |
| 2003/0130716 A1 | 7/2003 | Weber |

(56) References Cited

U.S. PATENT DOCUMENTS

| | | |
|---|---|---|
| 2003/0211258 A1 | 11/2003 | Sridharan et al. |
| 2004/0015183 A1 | 1/2004 | Lim et al. |
| 2004/0082965 A1 | 4/2004 | Beckham |
| 2004/0191442 A1 | 9/2004 | Lim |
| 2004/0199202 A1 | 10/2004 | Dubrul et al. |
| 2004/0254625 A1 | 12/2004 | Stephens et al. |
| 2005/0015048 A1 | 1/2005 | Chiu et al. |
| 2005/0038503 A1 | 2/2005 | Greenhalgh et al. |
| 2005/0267409 A1 | 12/2005 | Shkolnik |
| 2005/0273152 A1 | 12/2005 | Campbell et al. |
| 2006/0085024 A1 | 4/2006 | Pepper et al. |
| 2006/0136032 A1 | 6/2006 | Legarda |
| 2006/0161102 A1 | 7/2006 | Newcomb et al. |
| 2006/0271091 A1 | 11/2006 | Campbell et al. |
| 2007/0055301 A1 | 3/2007 | Campbell et al. |
| 2007/0061000 A1 | 3/2007 | Campbell et al. |
| 2007/0219489 A1 | 9/2007 | Johnson et al. |
| 2008/0125711 A1 | 5/2008 | Alpini et al. |
| 2008/0140173 A1 | 6/2008 | Eskaros et al. |
| 2008/0255507 A1* | 10/2008 | Mushtaha ............... 604/103 |
| 2008/0257155 A1 | 10/2008 | Bacino et al. |
| 2008/0312730 A1 | 12/2008 | Campbell et al. |
| 2009/0032470 A1 | 2/2009 | Bacino et al. |
| 2009/0053103 A1 | 2/2009 | Mortimer et al. |
| 2009/0283206 A1 | 11/2009 | Eskaros et al. |
| 2010/0049123 A1 | 2/2010 | Alpini et al. |
| 2010/0262178 A1 | 10/2010 | Alpini et al. |

FOREIGN PATENT DOCUMENTS

| | | |
|---|---|---|
| EP | 0 628586 | 12/1994 |
| EP | 737488 | 10/1996 |
| EP | 769307 | 4/1997 |
| EP | 0 829 269 | 3/1998 |
| GB | 1566674 | 5/1980 |
| NL | 1008178 | 8/1999 |
| WO | 90/14054 | 11/1990 |
| WO | 94/02185 | 2/1994 |
| WO | 95/05555 | 2/1995 |
| WO | 95/09667 | 4/1995 |
| WO | 95/17920 | 7/1995 |
| WO | 96/14895 | 5/1996 |
| WO | 96/40350 | 12/1996 |
| WO | 97/02791 | 1/1997 |
| WO | 97/40877 | 11/1997 |
| WO | 02/068011 | 9/2002 |
| WO | 03/000307 | 1/2003 |
| WO | 2008/021002 | 2/2008 |
| WO | 2008/021003 | 2/2008 |
| WO | 2008/021006 | 2/2008 |
| WO | 2008/021013 | 2/2008 |

* cited by examiner

CATHETER BALLOONS WITH INTEGRATED NON-DISTENSIBLE SEALS

CROSS REFERENCE TO RELATED APPLICATIONS

This application is a divisional application of commonly owned U.S. Ser. No. 11/501,149, filed Aug. 7, 2006, now abandoned.

BACKGROUND OF THE INVENTION

The present invention relates to balloon catheters and, more particularly, to a non-shortening wrapped balloon configured to expand with essential radial symmetry to a predetermined diameter upon application of a predetermined pressure thereto.

Balloon catheters are well known in the art. Such catheters are employed in a variety of medical procedures, including dilation of narrowed blood vessels, placement of stents and other implants, temporary occlusion of blood vessels, and other vascular uses.

In a typical application, the balloon is advanced to the desired location in the vascular system. The balloon is then pressure-expanded in accordance with a medical procedure. Thereafter, the pressure is removed from the balloon, allowing the balloon to contract and permit removal of the catheter. It is to be appreciated that the balloon is usually formed of an elastomeric material which is readily pressure-expanded, yet will also readily contract upon removal of the inflation pressure.

Procedures such as these are generally considered minimally invasive, and are often performed in a manner which minimizes disruption to the patient's body. As a result, catheters are often inserted from a location remote from the region to be treated. For example, during angioplasty procedures involving coronary vessels, the balloon catheter is typically inserted into the femoral artery in the groin region of the patient, and then advanced through such vessel into the coronary region of the patient. It is also common to have the length of the balloon change during inflation causing placement problems during procedures. Additionally, catheters have been unable to deliver balloons with large diameter expansion capability due to the need for a low profile and sustained pressures.

The present invention provides an improvement in balloon sealing techniques and reduction in seal profiles. Further, it is believed that further improvements in balloon performance can be achieved by modifying the mounting techniques, such as to provide a controlled failure mechanism.

SUMMARY OF THE INVENTION

The present invention provides catheter balloons comprising at least one balloon material and at least one integral non-distending region. The non-distending region comprises a plurality of layers which wind around the balloon material at a high angle of between 45 and 90 degrees relative to the longitudinal axis. The individual layers overlap at an opposing angle of between 45 and 135 degrees to the longitudinal axis upon inflation. The non-distending region is able to shape the balloon or provide an improved region to seal the balloon to a catheter upon inflation.

While the specific angles above are used as a general reference, the angle of the wrap can vary depending upon the desired attributes of the finished balloon. Several different areas of differing wrap angles may exist on one balloon. For instance, a continuous wrap may be utilized which forms a plurality of distensible balloon material passes which wind around the longitudinal axis at a lower angle than the angle observed for non-distending or less distensible regions of the balloon of the present invention. The less distensible regions may impart desired shape to the balloon, while the non-distending regions may be utilized to seal the balloon.

DETAILED DESCRIPTION OF THE INVENTION

The present invention describes a wrapped balloon with distensible and non-distensible regions suited for a seal on a catheter balloon. A catheter balloon of the present invention comprises at least one balloon material and at least one integral non-distending region comprising a plurality of non-distensible layers which wind around the balloon material. The non-distending regions comprise a plurality of layers which are wound around the balloon material at a high angle of between 45 and 90 degrees relative to the longitudinal axis. The individual layers overlap at an opposing angle of between 0 and 45 degrees to the longitudinal axis upon inflation. While the specific angles above are used as a general reference, the angle of the wrap can vary depending upon the desired attributes of the finished balloon. Several different areas of differing wrap angles may exist on one balloon. For instance, a continuous wrap may be utilized which forms a plurality of distensible balloon material layers which wind around the longitudinal axis at a lower angle than the angle observed for non-distending or less distensible regions of the balloon of the present invention. The less distensible regions may impart desired shape to the balloon, while the non-distending regions may be utilized to seal the balloon. The non-distending regions are incorporated or integrated into the surface of the balloon wall, into the balloon wall, or under the outer most surface of the balloon wall. The non-distending regions are in direct continuity with the balloon wall and are virtually indistinguishable in form from the balloon wall in an uninflated state. The non-distending regions are focal regions which are resistant to radial dilatation allowing for the sealing of an inflated balloon to an underlying catheter shaft or the imparting of non-cylindrical shapes to an inflated balloon.

Figure 1:
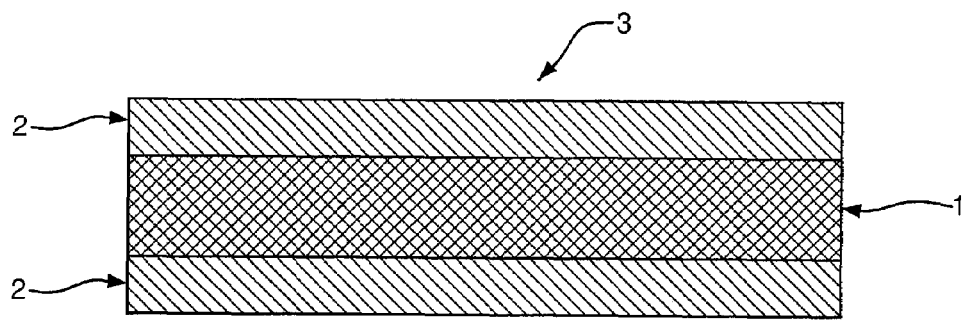
FIG. 1 shows a cross-section of a balloon material layer used to create a non-distensible seal.
Figure 2:
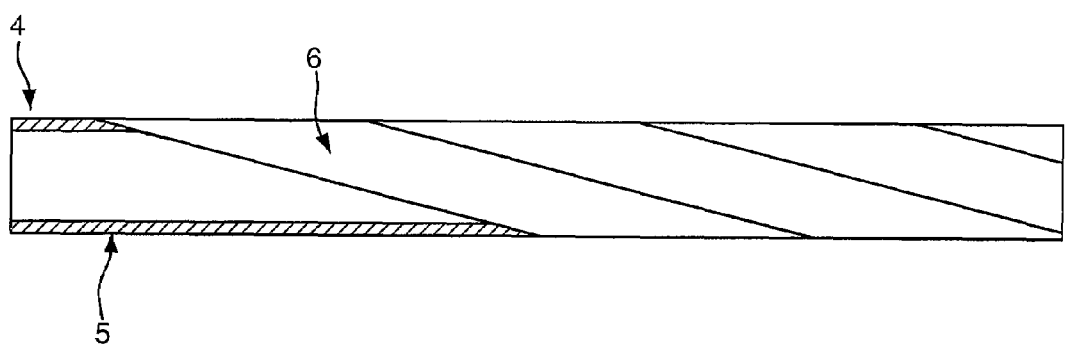
FIG. 2 shows a core wire with a fluoropolymer coating used to create a wrapped balloon.

FIG. 1 shows an example of a film used to create an integrated non-distensible seal on a balloon. By the term "non-distensible" it is meant that the material has a structure that is significantly less compliant under distention force than a distensible main body of the balloon and preferably the material will undergo little or no change in dimensions upon introduction of distention force. The balloons are created by wrapping material layers into passes circumferentially about a longitudinal axis. An individual pass is comprised of one or more layers of material which are laid at similar angles in relation to the longitudinal axis of the balloon. A layer is considered to be one thickness of balloon material which may be wrapped, folded, laid or weaved over, around, beside or under another thickness. A longitudinal pass comprises a distinctive layer or series of layers of material which are wound to form a region or area distinct from surrounding or adjoining parts. For instance, a pass may comprise multiple layers of balloon material wrapped at a 90 degree angle relative to the longitudinal axis. This exemplary pass may then be flanked by layers of balloon material wrapped at dissimilar angles in relation to the longitudinal axis, thus defining the boundary of the 90 degree angle wrapped pass. It is important to note that a pass may span the entire length of the balloon or may in certain instances, such as non-distending regions, span only a partial length of the balloon. The balloon material layers in FIG. 1 comprise a composite film 3 which is then wrapped to form the balloon structure. The balloon material layers may comprise a laminate, elastomer, fluoropolymer, low modulus polymer, PEBA, a highly oriented fibrous reinforcing polymer such as PTFE or expanded PTFE (ePTFE), polyolefin, polyester, polyamide, nylon or any other suitable material or combination of materials. The balloon material layer may be wrapped in a manner to incorporate a wrapped or integrated seal into the balloon structure using a continuous strand of a single composite film or material for both the balloon material layer and the at least one integral non-distending region. Alternatively, the balloon material layer may be a different material from the non-distending region wrap material. Suitable non-distensible region wrap materials include fibers, metals, wires, bands, elastomers, or any other suitable non-distensible seal materials or combinations of materials.

In one embodiment of the present invention, the balloon material and the non-distending region wrap material are comprised of the same film. The film is a composite film comprised of a membrane 1 and a coating 2. The membrane may be made in accordance with the general teachings of U.S. Pat. No. 5,476,589 or U.S. patent application Ser. No. 11/334,243. In one preferred embodiment, an ePTFE membrane 1 is longitudinally expanded to a ratio of 80 to 1, and more preferably 55 to 1. The preferred membrane 1 is further transversely expanded to a ratio of 20 to 1 and more preferably 2.25 to 1, to produce a thin strong membrane. Isotropic films may also be employed to create a non-distensible seal. The mass and thickness of the membrane can vary depending upon the desired application. The membrane is coated with a sealing material to imbibe the matrix of the membrane and produce a composite film with an extended sealing material coating on one or both sides of the membrane to form an imbibed ePTFE membrane. In one preferred embodiment the membrane alone exhibits a mass of approximately 2.0 to 6.5 g/m$^2$, preferably 2.7 to 4.5 g/m$^2$ and a tensile strength may vary but is preferably of between 3.9 and 7.6 lbs./inch. In certain embodiments, it may be desirable to have increased tensile strengths exceeding 7.6 lbs./inch. Thickness of the membrane may also range, but is preferably between 2.5 to 10 micrometers.

As shown in FIG. 1 when an imbibed composite film 3 is used, it is desirable that the membrane comprises open spaces throughout the entire membrane, such as an ePTFE membrane, or other material comprising an open matrix. It is also preferable that the sealing material is an elastomer, polyurethane, polymer coating, styrenic block copolymer, adhesives or other suitable material. In one preferred embodiment, the sealing material is a polyurethane. The coated membrane produces a composite film with an amount of a sealing material forming a coating on at least one side of the membrane and the remainder of the sealing material imbibed throughout the membrane. The total polymer weight application may range, but in one preferred embodiment is between 40% to 60% of the total final composite film weight.

Figure 3:
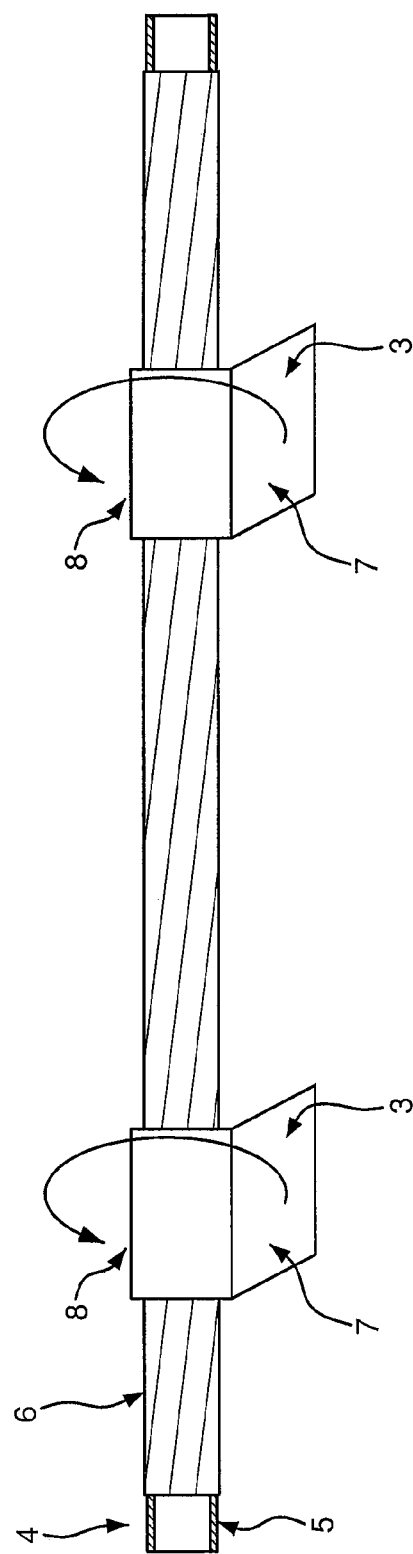
FIG. 3 shows balloon with a non-distending seal present on the exterior of a balloon material layer.
Figure 4:
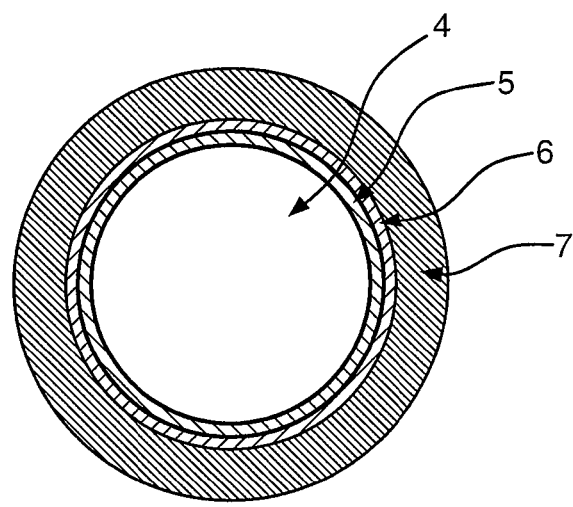
FIG. 4 shows a cross-section of a balloon with a non-distending region formed between balloon layer materials.
Figure 5:
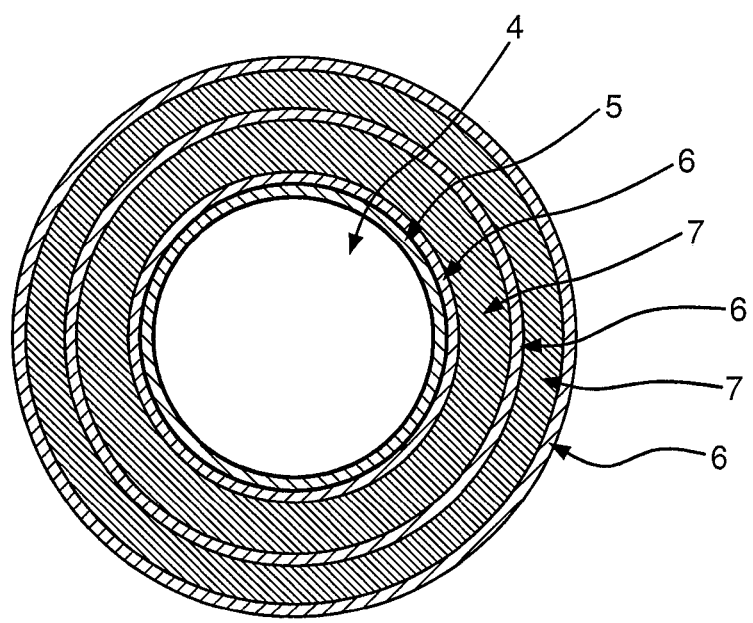
FIG. 5 shows a cross-section of the layer construction of a balloon with multiple non-distending regions formed between balloon layer materials.
Figure 6:
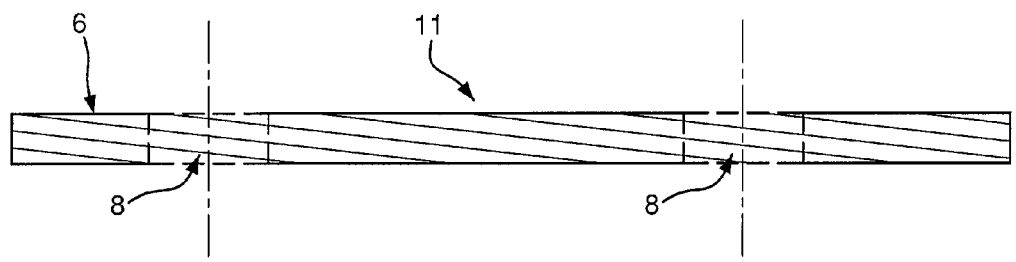
FIG. 6 shows an uninflated shaped composite balloon with non-distending regions formed between balloon layer materials.
Figure 7:
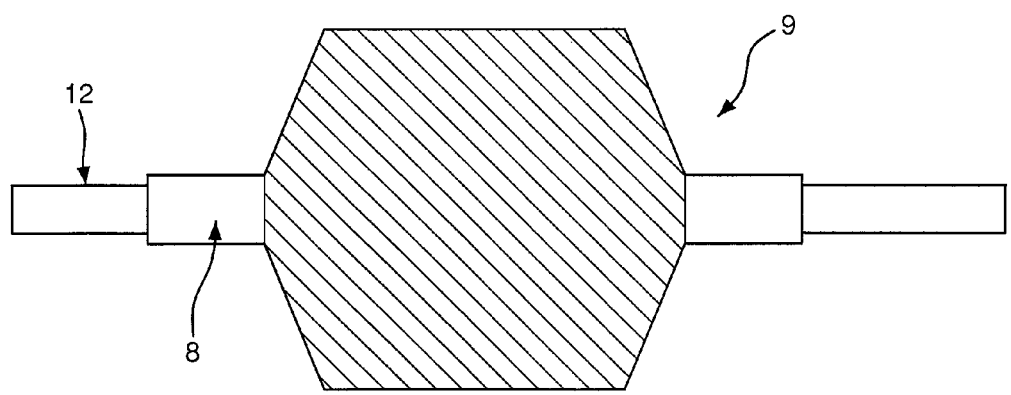
FIG. 7 shows a catheter balloon at a final diameter with non-distensible regions.

FIGS. 2-8 show a core wire 4 which may be coated with a release coating 5 (as shown) and then wrapped with a balloon material layer 6. As shown in FIG. 3, a composite film 3 is slit to a narrow width (i.e., 1-10 mm), and then wrapped around a balloon material layer a plurality of times to result in a non-distensible seal forming a non-distensible region 8. A cross-section of a non-distensible layer 7 is shown in FIG. 4. The core wire 4 is coated with a release coating 5 then wrapped with balloon material layer 6 and non-distensible layer 7. In one embodiment shown in FIGS. 3 and 4, the non-distensible region 8 is formed by wrapping a discontinuous longitudinal region of balloon with a film a plurality of times at an angle of approximately 90 degrees from the longitudinal axis over-top of a distensible layer 6 of composite film 3 wrapped at a low angle of between 2 to 45 degrees and preferably of between 4 to 5 degrees from the longitudinal axis. The non-distensible layer 7 of composite film may be sized and/or wrapped to a desired width on the balloon to form the non-distensible regions 8. The non-distensible layer 7 of composite film may be comprised of different widths, thickness or types of film in various desired locations. The film making up the balloon and the film making up the non-distensible layer may be the same material. Shear strength is increased by the use of wider films as balloon material which provides more interfacing surface area. This increased shear strength allows the non-distensible seals to provide an increase in seal strength and consequentially increase balloon catheter pressure capability, as compared to traditional seals. To further increase the shear strength, the non-distensible layers 7 of the non-distensible regions 8 may be oriented between layers of balloon material as shown in FIGS. 5 and 6 respectively. The core wire 4 is wrapped with a balloon material layer 6 and non-distensible layer 7 and then repeated. The non-distensible layer(s) also provides homogenous distribution of pressure upon inflation of the balloon. In the event of a rupture, the non-distensible regions manifest a desirable diffused burst pressure and non-catastrophic seal failure. It is further desirable that the balloon and the non-distensible regions are comprised of compatible materials with the same or approximately the same tensile properties or adhesive compatible. The individual non-distending layers of the non-distending region may be askew, at opposing high angles of 45 to 90 degrees from the longitudinal axis, or may be aligned with each other.

If desired, the balloon material with non-distensible regions may be heated to set the angles of film at their wrapped state and fuse the multiple layers together. The above embodiment describes a continuous composite film wrapped at varying angles to form an inflatable balloon with both distensible and non-distensible regions.

Alternatively the non-distensible regions may be comprised of a second material that is not similar to the balloon material. The non-distensible layers which form the non-distensible regions, may be between balloon material layers or alternatively may be in contact with only one balloon material layer.

In another aspect, the catheter shaft may comprise grooves or ridges in either a vertical, horizontal or helical relation to the longitudinal axis. These ridges function to enhance the seal strength of the non-distensible seal by providing increased surface area on shaft for binding. The ridges also enhance the texture of the shaft to increase the surface friction required to initiate movement of the non-distensible areas upon inflation.

The core wire 4 may comprise a release coating 5 over the core wire and both may be removed from the composite balloon construction. As shown in FIG. 6, the shaped composite balloon 11 may be wrapped and then cut on the non-distensible regions 8. The non-distensible regions 8 may then be mounted on a catheter shaft 12 to produce an individual catheter balloon 9 of wrapped balloon shown in the inflated state, in FIG. 7.

Figure 8:
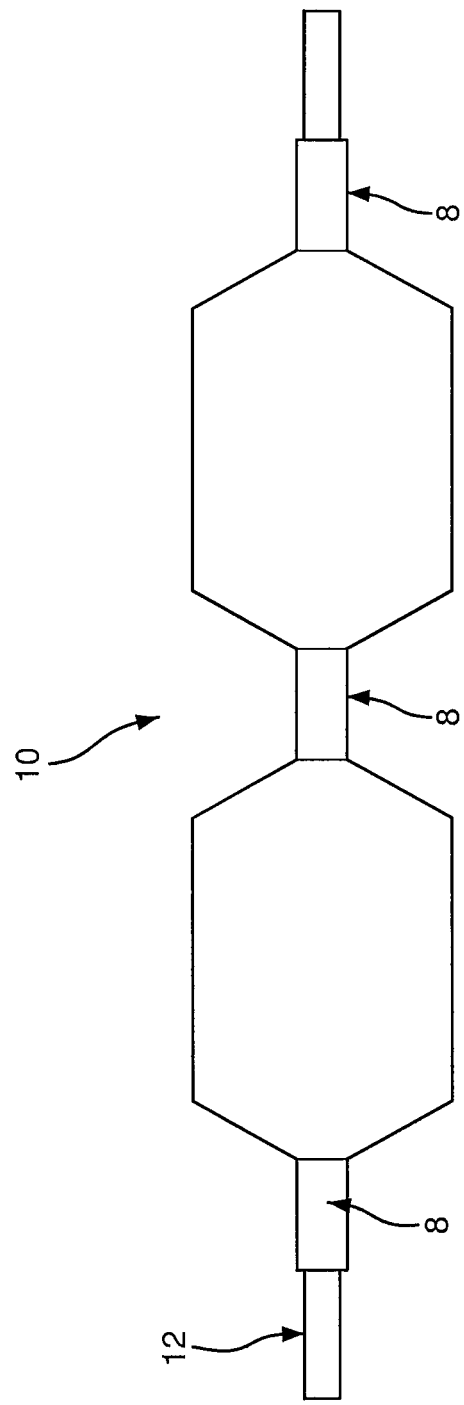
FIG. 8 shows multiple catheter balloons formed in a single structure and separated by non-distensible regions.

The shaped catheter balloon 11 may be formed in the same manner as described above but fashioned so that multiple shaped catheter balloons are formed on a single wire, FIG. 8. The multiple shaped catheter balloons are separated from each other by a non-distensible region 8. The non-distensible regions between the individual balloons may further be cut to produce individual shaped catheter balloons 10 with non-distensible regions 8 at each end as depicted in FIG. 8.

The present invention provides balloon catheters with a non-distending region located between two or more balloon material layers or on the surface of a balloon material. The balloon catheter may have a plurality of non-distending regions present forming a plurality of non-distending layers. The balloon catheter may further be fashioned to include a plurality of non-distending regions which impart a shape to the balloon material upon inflation. The non-distending regions may impart a form to the balloon that renders the balloon non-cylindrical. It is also possible to incorporate a non-distending region of varying widths and thicknesses. For instance, the non-distending region may be desired to be either wider or narrower than the final diameter of the balloon.

The non-distending regions are described herein as a film. However, the non-distending regions may be made of any suitable non-compliant material including but not limited to metal wire, monofilament fibers, and extruded tubes. In one desired application polytetrafluoroethylene is wrapped in layers so that an angle of between 45 and 90 degrees is achieved upon inflation, thus sealing the balloon. In a preferred embodiment, the non-distending regions comprise an elastomer imbibed polytetrafluoroethylene material suitable to seal the withstand inflation pressures without distending upon balloon inflation.

A continuous integrated seal on an inflatable balloon may be formed by using or providing a first balloon material pass which is configured to form a desired balloon shape. The balloon shape is then wrapped with a wrap pass around said first balloon material pass so that the angle of the wrap changes to wrap at least one pass at an angle sufficient to create a non-distending region over the first balloon material pass. A second balloon material is then wrapped around a non-distending region to increase the bonding surface area of a non-distending region; and form an integrated seal upon inflation. In this manner, it is believed that a non-distending region is located between two balloon materials to increase the bonding surface area and provide a gentle failure mode upon over pressurization of the balloon.

A method of forming a continuous exposed integrated seal on an inflatable balloon is also provided. The balloon material is configured to form a desired balloon shape; and then wrapped with at least two passes of a first balloon material. The wrap angle is then changed to wrap one pass at an angle to the next pass sufficient to create a non-distending region. The non-distending region on the balloon material provides an integrated seal on an inflatable balloon A method is provided for forming a discontinuous non-exposed integrated seal on an inflatable balloon. A balloon material is wrapped in at least two opposing angle passes to form a first wrap. Then at least one pass of a second wrap is wrapped around the first wrap at an angle sufficient to create a non-distending region over a balloon material layer. At least one pass of a third wrap of balloon material is wrapped around the non-distending region to increase the bonding surface area of the non-distending region, and forms an integrated non-distending region in an inflatable balloon. The non-distending region formed may be a seal region or a region which contours the inflated balloon.

A method of forming a discontinuous exposed integrated seal on an inflatable balloon is also provided. A balloon material is wrapped in at least two opposing angle passes to form a first wrap. Then at least one pass of a second wrap is wrapped around the first wrap at an angle sufficient to create a non-distending region over a first balloon material layer, thus forming an integrated seal region on an inflatable balloon.

While particular embodiments of the present invention have been illustrated and described herein, the present invention should not be limited to such illustrations and descriptions. It should be apparent that changes and modifications may be incorporated and embodied as part of the present invention within the scope of the following claims. Wrapped balloons may be constructed with our without a bladder between the FEP coating 5 and the balloon material 6.

EXAMPLES

Example 1

Composite Film

The ePTFE membrane used to make the composite film was made in accordance with the teaching in U.S. Pat. No. 5,476,589 to Bacino. Specifically, the ePTFE membrane was longitudinally expanded to a ratio of 55 to 1 and transversely expanded approximately 2.25 to 1, to produce a thin strong membrane with a mass of approximately 3.5 g/m$^2$ and a thickness of approximately 6.5 micrometers.

The composite film was made by using a wire-wound rod coating process whereby a solution of Tecothane TT-1085A polyurethane (Thermedics, Inc, Woburn, Mass.) and tetrahydrofuran (THF) was coated onto an ePTFE membrane. A 3% to 8% by weight solution of Tecothane TT-1085A polyurethane in THF was coated onto the ePTFE membrane to produce a composite film with approximately equal amounts of Tecothane TT-1085A polyurethane as depicted in FIG. 1 on either side and throughout the ePTFE membrane and a total polymer weight application of approximately 40% to 60% of the total final composite film weight.

Example 2

Non-Distensible

The composite film was slit to 5 mm wide and wrapped around a 30.5 cm long core wire (Putnam Plastics LLC, Dayville, Conn.) at a 4 to 5 degree angle from the longitudinal axis of the wire. The core wire was a 0.2 mm diameter silver plated copper wire with a fluoroethylene-propylene (FEP) 5100 coating that resulted in a final wire diameter of with a 0.394 mm. The core wire was then wrapped with the composite film in the opposite direction at a 4 to 5 degree angle from the longitudinal axis of the wire.

The first balloon material layer was then over-wrapped with a non-distensible layer of composite film slit to 10 mm wide to form the non-distensible regions. The 10 mm wide second wrap layer of composite film was wrapped around the first balloon material layer in two locations, approximately 50 mm apart. The 10 mm wide composite film was wrapped around the first balloon material five times at an angle of approximately 90 degrees from the longitudinal axis, or around the circumference of the balloon.

The 5 mm wide composite film was then wrapped around the core wire at a 4 to 5 degree angle from the longitudinal axis of the wire. The core wire was then wrapped with the composite film in the opposite direction at a 4 to 5 degree angle from the longitudinal axis of the wire. This process was repeated until four passes of low angle wrap were completed.

The 10 mm wide composite film was then again wrapped around the balloon material layer at a an angle of approximately 90 degrees from the longitudinal axis five times in the same locations as previously wrapped, 50 mm apart.

Finally, the 5 mm wide composite film was again wrapped around the core wire at a 4 to 5 degree angle from the longitudinal axis of the wire. The wire was then wrapped with the composite film in the opposite direction at a 4 to 5 degree angle from the longitudinal axis of the wire. This process was repeated until four passes of low angle wrap were completed. The wrapped wire was then heated for approximately 30 minutes at 180° C. in a convection oven.

The core wire and the FEP coating over the core wire were removed from the composite balloon with non-distensible regions. Approximately a 2.54 cm long section of the composite balloon was removed from either end of a 30.5 cm long section of the balloon over core wire construction. The exposed ends of the core wire were clamped with hemostats and pulled by hand until the core wire had been stretched approximately 5 cm, at which point it was removed from the center of the tube. The FEP coating was removed in a similar fashion, but was stretched approximately 50 cm before it was removed from the balloon. The composite balloon was cut in the center of each 10 mm wide non-distensible region to produce a 3 mm diameter composite balloon with 5 mm wide non-distensible regions at each end as depicted in FIG. 6

Example 3

Shaped Non-Distensible

The composite film was slit to 5 mm wide and wrapped around a 30.5 cm long core wire (Putnam Plastics LLC, Dayville, Conn.) at a 4 to 5 degree angle from the longitudinal axis of the wire. The core wire was a 0.2 mm diameter silver plated copper wire with a fluoroethylene-propylene (FEP) 5100 coating that resulted in a final wire diameter of with a 0.394 mm. The core wire was then wrapped with the composite film in the opposite direction at a 4 to 5 degree angle from the longitudinal axis of the wire.

The first balloon material layer was then over-wrapped with a non-distensible layer of composite film slit to 10 mm wide to form the non-distensible regions. The 10 mm wide second wrap layer of composite film was wrapped around the first balloon material layer in three locations, approximately 50 mm apart. The 10 mm wide composite film was wrapped around the first balloon material five times at an angle of approximately 90 degrees from the longitudinal axis, or around the circumference of the balloon.

The 5 mm wide composite film was then wrapped around the core wire at a 4 to 5 degree angle from the longitudinal axis of the wire. The core wire was then wrapped with the composite film in the opposite direction at a 4 to 5 degree angle from the longitudinal axis of the wire. This process was repeated until four passes of low angle wrap were completed.

The 10 mm wide composite film 3 was then again wrapped around the balloon material layer at a an angle of approximately 90 degrees from the longitudinal axis five times in the same three locations as previous wrapped, 50 mm apart.

Finally, the 5 mm wide composite film was again wrapped around the core wire at a 4 to 5 degree angle from the longitudinal axis of the wire. The wire was then wrapped with the composite film in the opposite direction at a 4 to 5 degree angle from the longitudinal axis of the wire. This process was repeated until four passes of low angle wrap were completed. The wrapped wire was then heated for approximately 30 minutes at 180° C. in a convection oven.

The core wire and the FEP coating over the core wire were removed from the composite balloon construction with non-distensible regions. Approximately a 2.54 cm long section of the composite balloon was removed from either end of a 30.5 cm long section of the balloon over core wire construction. The exposed ends of the core wire were clamped with hemostats and pulled by hand until the core wire had been stretched approximately 5 cm, at which point it was removed from the center of the tube. The FEP coating was removed in a similar fashion, but was stretched approximately 50 cm before it was removed from the balloon. The composite balloon was cut in the center of the outer 10 mm wide non-distensible regions to produce a 3 mm diameter shaped catheter balloon with 5 mm wide non-distensible regions at each end and a 10 mm wide non-distensible region in the center.

The invention claimed is:

1. A balloon catheter comprising a catheter shaft and a catheter balloon comprising at least two layers of at least one balloon material and at least one non-distending region comprising a plurality of elastomer-imbibed polytetrafluoroethylene layers in between the at least two layers of balloon material which wind around the balloon material and overlap to form an angle of between 0 and 90 degrees relative to each other upon inflation and retain pressure in the balloon, wherein said elastomer-imbibed polytetrafluoroethylene comprises a film of said elastomer on both sides and throughout said polytetrafluoroethylene.

2. The balloon of claim 1 wherein the catheter shaft comprises ridges in contact with the integral non-distending region of the balloon.

3. The balloon catheter of claim 1, wherein there are at least three non-distending regions in said balloon catheter.

4. The balloon catheter of claim 3, wherein said balloon is a shaped balloon.

5. The balloon catheter of claim 1, wherein said balloon material and material comprising the non-distending region are fused together to create a continuous composite.

6. The balloon catheter of claim 1, wherein said elastomer is a polyurethane.

* * * * *